June 26, 1973 H. YAHEL Plant Pat. 3,366
WHITE NARCISSUS
Filed Feb. 3, 1972
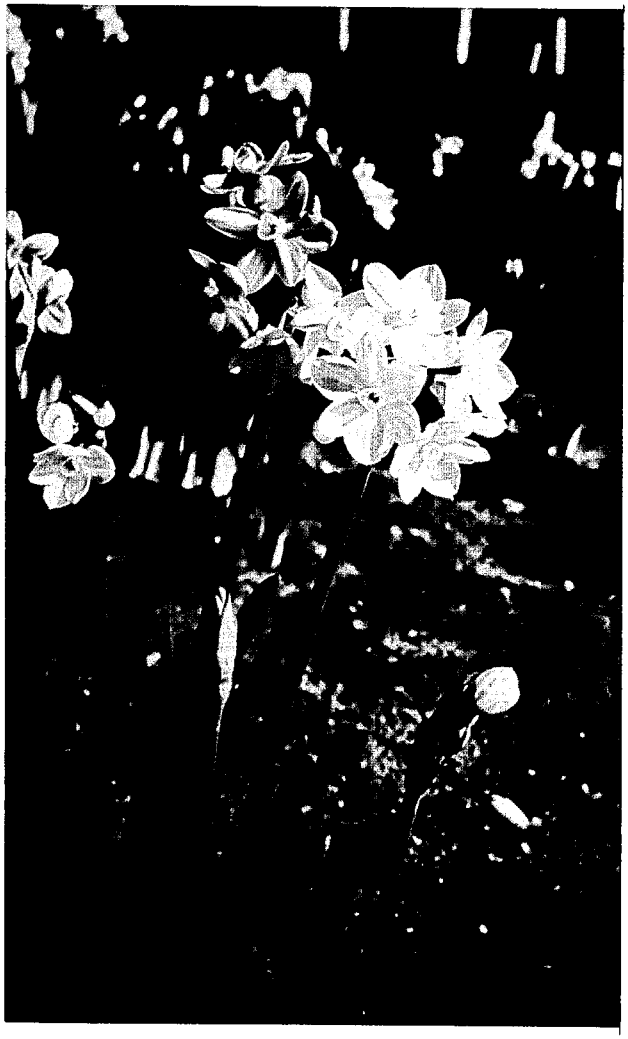

United States Patent Office

Plant Pat. 3,366
Patented June 26, 1973

3,366
WHITE NARCISSUS

Herut Yahel, Rishon Lezion, Israel, assignor to The State of Israel, Ministry of Agriculture, Jerusalem, Israel Filed Feb. 3, 1972, Ser. No. 223,377
Int. Cl. A01h 5/00
U.S. Cl. Plt.—68 1 Claim

ABSTRACT OF THE DISCLOSURE

A new variety of white narcissus, sub-genus Tazetta, originating from Narcissus Paperwhite and having desired properties especially as regards growth capacity, propagative characteristics, blooming ability, earliness of blooming, flower size and form and stem strength.

BACKGROUND OF THE INVENTION

The new variety of white narcissus was developed by me as a seedling of two unlabelled Narcissus Paperwhite parents. It was raised and vegetatively propagated by splitting in the fields of the Agricultural Research Organisation Volcani Centre, a department of the Ministry of Agriculture of the Government of Isreal, at Bet Dagan, Israel.

The new variety has proved to be superior to its parents, the common Narcissus Paperwhite, in many respects. It is very floriferous and has big flowers and a well shaped inflorescene. It has better and quicker growth and is a good vegetative propagator and a strong plant.

DESCRIPTION OF THE DRAWING

The new variety of narcissus is shown in the accompanying photographic drawing which shows the full opened flowers in full color, their form and disposition on the stem.

DESCRIPTION OF THE NEW VARIETY

General characteristics

The known variety closest to the new variety is the common Narcissus Paperwhite. The characteristics of the new variety are, therefore, compared with the known variety aforesaid.

The new variety produces a strong plant, is quick to develop, it is a good propagator, and can be used as a pot plant as well as a cut flower. The leaves are erect.

Like the known Narcissus Paperwhite and most Tazettas, the new variety is an indoor plant in cooler countries where temperatures drop below freezing point in winter. It can be grown in the open air in warmer climates like that of most Mediterranean countries.

The new variety was tested in the cooler climate of Holland. Bulbs planted in a greenhourse by the middle of October and grown at a temperature of 13–16° C., produced plants that reached blooming by the end of the first quarter of December. The new variety is thus especially suitable for Xmas blooming.

The odor is strong and sweet.

The new variety belongs to Division 8 according to the Royal Horticulture Society classification.

*The bulb*

This is short-necked, wrapped in brown skin and somewhat angular in shape. It is similar in shape to that of Narcissus Paperwhite, but owing to more splitting of the main bulb, many bulbs are not ideally round and look somewhat angular.

*Blooming*

The flowers are white and bigger than those of Narcissus Paperwhite. Their diameter reaches about 45 mm.

The external petals are slightly wider than the internal ones. They are broad and round and their free end is pointed. Both the outer and inner petals are wider than those of Narcissus Paperwhite. The midrib of the petals is thicker and higher than the rest of the tissue and forms a ridge along the midrib. The crown is medium sized, almost round, as contrasted to that of Narcissus Paperwhite which is somewhat triangular.

The pollen grains are bright yellow, similar to those of Narcissus Paperwhite.

The pistil is taller than the upper set of stamens, as distinct from Narcissus Paperwhite in which the pistil is approximately as long as the stamens. The inflorescence is well-shaped. Under favorable climatic conditions, like those prevailing in Isreal, each bulb is apt to produce more than one floriferous stem.

*The stem*

This is strong and erect, almost round transversely. When flower picking is the aim, the stem can easily be pulled from the depth, inside the bulb, including the white part of the subsoil stem. The stem is higher than the leaves at blooming, reaching a height of about 25 cm. from the soil to the base of the bract, when the flowers first open; it adds 1–1.5 cm. to its height each day. The aforesaid indications regarding the stem are valid for open-air cultivation under climatic conditions like those of Isreal.

*The leaves*

They are brighter than the leaves of Narcissus Paperwhite. The leaves go on growing from the time of sprouting until shortly before the termination of the growth of the plant. Their length at blooming is influenced by the date of planting. Under open-air conditions like those of Isreal, early planting (September) produces greater length of the leaves than later planting (December). However, the leaves are shorter than the stems at the time of anthesis.

*Propagation*

The new variety propagates well, which means that it produces comparatively many daughter bulbs by splitting, when grown in the field in a region where climatic conditions enable outdoor growing.

I claim:

1. A new and distinct variety of white narcissus plant, substantially as herein described and shown, most nearly resembling Narcissus Paperwhite and characterized, as compared with and distinct from Narcissus Paperwhite, by bigger flowers which have broad, roundish, pointed petals and whose pistils are larger than the stamens, and by earlier blooming.

No references cited.

ROBERT E. BAGWILL, Primary Examiner